United States Patent
Rhein et al.

(10) Patent No.: US 8,764,722 B2
(45) Date of Patent: Jul. 1, 2014

(54) ABSORBENT ARTICLE WITH CUSHIONED WAISTBAND

(75) Inventors: Christina Marie Rhein, Oshkosh, WI (US); Daniel Lee Ellingson, Singapore (SG); Connie May McMorrow, Menasha, WI (US); John Timothy Hahn, Merrill, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 519 days.

(21) Appl. No.: 13/096,031

(22) Filed: Apr. 28, 2011

(65) Prior Publication Data

US 2012/0277703 A1 Nov. 1, 2012

(51) Int. Cl.
*A61F 13/15* (2006.01)

(52) U.S. Cl.
USPC .............. 604/385.29; 604/385.3; 604/385.28; 604/385.24; 604/385.27

(58) Field of Classification Search
USPC ............... 604/385.29, 385.28, 385.3, 385.24, 604/385.27
See application file for complete search history.

(56) References Cited

U.S. PATENT DOCUMENTS

| | | | |
|---|---|---|---|
| 3,572,342 A | 3/1971 | Lindquist et al. |
| 4,425,129 A | 1/1984 | Karami |
| 4,657,539 A | 4/1987 | Hasse |
| 4,861,652 A | 8/1989 | Lippert et al. |
| 4,978,570 A | 12/1990 | Heyn et al. |
| 5,489,282 A | 2/1996 | Zehner et al. |
| 5,613,961 A | 3/1997 | Dipalma et al. |
| 5,649,918 A | 7/1997 | Schleinz |
| 5,653,843 A | 8/1997 | Fell et al. |
| 5,797,824 A | 8/1998 | Tracy |
| 5,868,725 A | 2/1999 | Coles et al. |
| 6,159,191 A | 12/2000 | Mishima et al. |
| 6,254,583 B1 | 7/2001 | Coates |
| 6,881,207 B1 | 4/2005 | Tracy |
| 7,316,674 B2 | 1/2008 | Infantino et al. |
| 2005/0095942 A1 | 5/2005 | Mueller et al. |
| 2006/0058767 A1* | 3/2006 | Zhang et al. ............. 604/385.24 |
| 2006/0206071 A1* | 9/2006 | Graef et al. ................... 604/365 |
| 2008/0287899 A1 | 11/2008 | Morrell-Schwartz et al. |
| 2010/0298796 A1 | 11/2010 | Horn et al. |

FOREIGN PATENT DOCUMENTS

| | | |
|---|---|---|
| EP | 0 219 969 A1 | 4/1987 |
| EP | 0 235 014 B1 | 7/1991 |
| EP | 0 588 860 B1 | 12/1995 |
| EP | 0 613 361 B1 | 1/1997 |
| EP | 2 087 871 A1 | 8/2009 |
| GB | 2 101 468 A | 1/1983 |
| WO | WO 95/05140 A1 | 2/1995 |

* cited by examiner

*Primary Examiner* — Jacqueline F. Stephens
(74) *Attorney, Agent, or Firm* — Kimberly-Clark Worldwide, Inc.

(57) ABSTRACT

A waistband structure for an absorbent article is disclosed. The waistband structure extending across at least one of the front and back waist regions and is composed of a filler material and a waistband material positioned over the filler material. The waistband structure may be bonded to at least one of the front and back waist regions via a bond pattern. The bond pattern may vary position in the longitudinal direction and have at least one peak and one valley across the respective waist region. Typically, a distance between the peak and the valley in the bond pattern is between 5 and 100 mm. The bond pattern results in a z-directional height of the waistband structure varying on the respective waist region.

19 Claims, 4 Drawing Sheets

ABSORBENT ARTICLE WITH CUSHIONED WAISTBAND

BACKGROUND

Various types of disposable absorbent articles such as disposable diapers, child's training pants, diaper pants, disposable swim pants, incontinence articles, and the like, utilize a chassis incorporating an absorbent system and an elastomeric waistband. The waistband provides for enhanced fit, comfort to the wearer, and improved product performance.

Various elastomeric waistband configurations have been developed for use with disposable absorbent products. For example, various pull-on pant-like articles have gathered elastic waistband portions. Some disposable absorbent garments have an elastic waistband with an elastic element joined in a stretched condition to a marginal portion of an exterior panel of the garment with a plurality of spaced bond points. These typical diaper configurations include elasticized waistband portions and tape members extending from the side margins of the back waist region. The tape members include a fastening strip, such as a hook-type material, that attaches to a corresponding landing pad material provided on the front waist region to secure the article to a wearer.

Conventional elastomeric waistband configurations may, however, be improved upon and provide a more comfortable fit for a wearer and improved leakage protection.

SUMMARY

In general, an absorbent article incorporating a unique waistband configuration for use in a variety of absorbent articles, such as disposable diapers, child's training pants, incontinence articles, diaper pants, disposable swim pants, and the like, is disclosed herein.

An absorbent article including a chassis having a front waist region, a back waist region, and a crotch region extending between the front and back waist regions; an outer cover member and a bodyside liner extending between the front and back waist regions is disclosed. An absorbent body structure between the outer cover member and the bodyside liner is included. A waistband structure extending across at least one of the front and back waist regions may be composed of a filler material and waistband material. The waistband structure may be bonded to at least one of the front and back waist regions via a bond pattern. The bond pattern results in a z-directional height of the waistband structure varying on the respective waist region.

The waistband material may be either an elastomeric material or a non-elastomeric material. Desirably, the waistband material comprises an elastomeric material.

In one embodiment, the elastomeric material positioned over the filler material is provided. In other embodiments the waistband structure may be an integral structure composed of both a filler material and an elastomeric material.

The filler material may be selected from lofty nonwoven materials, laminates, spunbond fabrics, films, meltblown fabrics, elastic netting, microporous web, bonded carded webs, absorbent core materials, surge materials, or foams comprised of elastomeric or polymeric materials, and combinations thereof. Desirably, the filler material is a lofty nonwoven material.

As described above, the waistband structure is attached to at least one of the front and back waist regions via a bond pattern. The bond pattern may vary position in the longitudinal direction and have at least one peak and one valley across the respective waist region. Typically, a length between the peak and the valley in the bond pattern is between 5 and 100 mm.

The bond pattern may be a repeating wave pattern selected from a sinusoidal, triangle, square or sawtooth pattern. The bond pattern may be a pattern of discrete bond points, wherein a distance between successive bond points is less than about 10 mm, and more desirably between about 1 and about 5 mm.

The absorbent article may also have a waist pocket flap extending from the waistband structure which includes a substantially fixed edge portion secured to the waist region of the absorbent article and a movable edge portion, which is typically longitudinally spaced from the fixed edge portion by a selected distance.

The waistband structure may also be bonded to at least one of the front and back waist regions via multiple series of bond patterns. Each series of bond patterns may be a wave pattern across the respective waist region.

BRIEF DESCRIPTION

DETAILED DESCRIPTION

In general, a unique waistband configuration for use in a variety of absorbent articles, such as disposable diapers, child's training pants, incontinence articles, diaper pants, disposable swim pants, and the like, is disclosed herein. For purposes of description only, embodiments of an absorbent article according to the invention will be made with reference herein to a disposable diaper. It should be understood that the invention is not limited to disposable diapers. Aspects of the invention are explained below by reference to embodiments of a disposable diaper. As mentioned, the invention is not limited to diapers, and as utility for various other absorbent articles, including, training pants, swim pants, incontinence articles, and the like.

Figure 1:
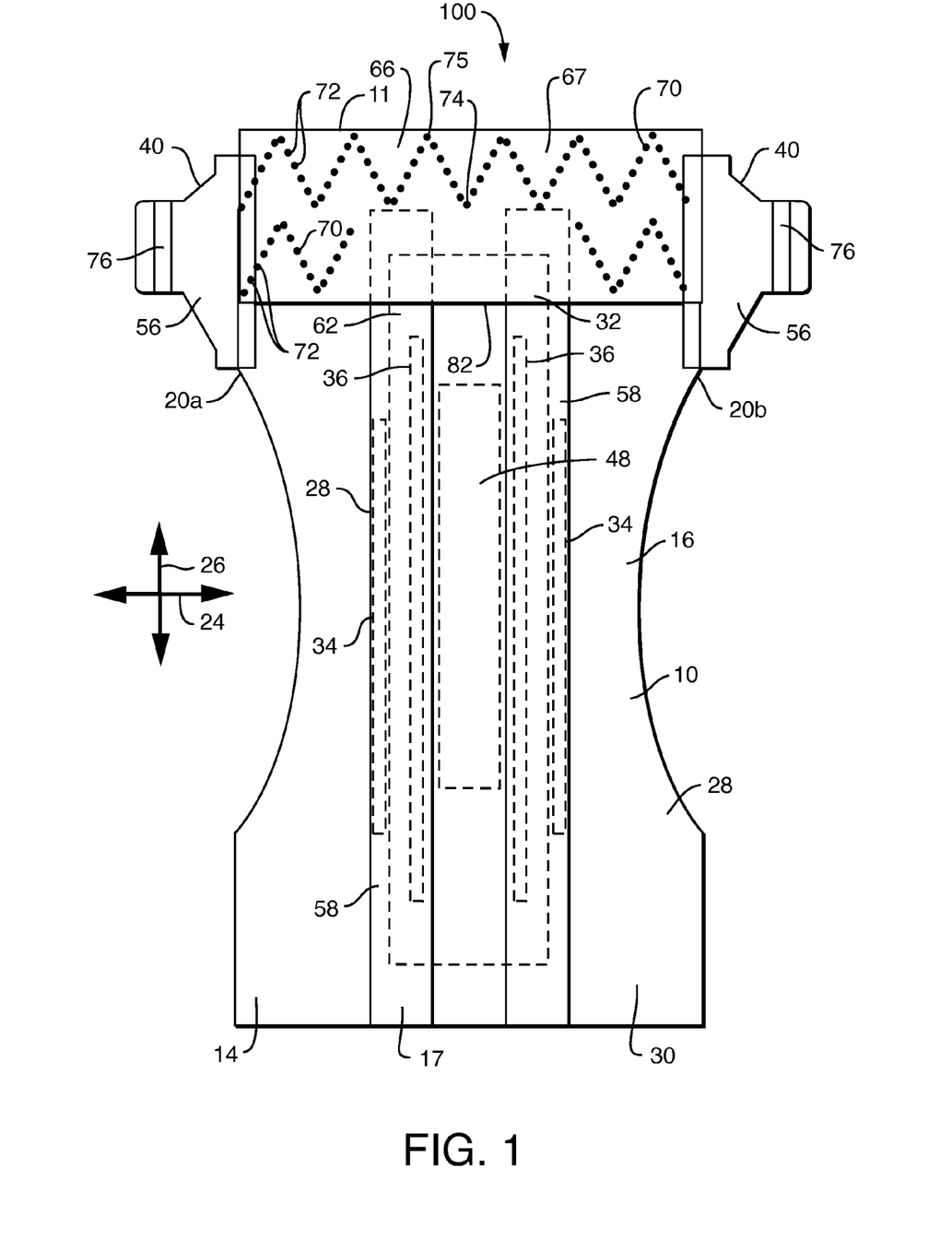
FIG. 1 illustrates a bodyside plan view of an absorbent article having a unique waistband structure as described herein.
Figure 2:
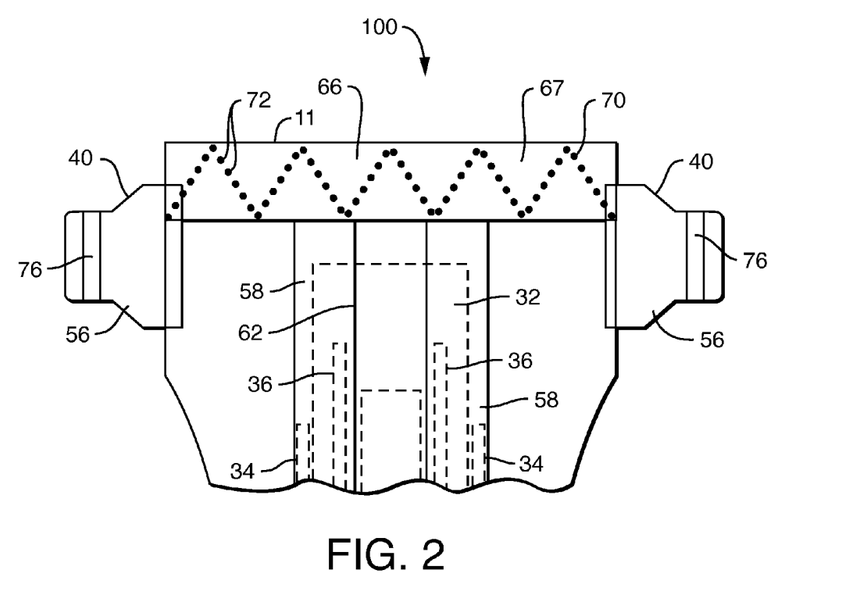
FIG. 2 illustrates a partial bodyside plan view of the waistband region of the absorbent article in FIG. 1.

FIG. 1 shows a body facing plan view of a representative article 100, in this case a disposable diaper, in its generally flat-out, uncontracted state (i.e., with substantially all elastic induced gathering and contraction removed). The article components are attached or joined together by conventional suitable attachment methods such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the various components.

With reference to the Figures in general, the representatively shown diaper article 100, is illustrated. The article 100 includes a body or chassis 10 having lateral sides 20a and 20b, a lengthwise, longitudinal direction 24, a lateral, transverse cross-direction 26, a front waist region 14, a back waist region 12, and an intermediate crotch region 16 interconnecting the front and back waist regions. The waist regions 12 and 14 comprise those portions of the article 100 which when worn, wholly or partially cover or encircle the waist or mid-lower torso of the wearer. The front 14 and back 12 waist regions have front and back waistband portions 17, 11. The intermediate crotch region 16 lies between and interconnects the waist regions 14 and 12, and comprises that portion of the article 100 which, when worn, is positioned between the legs of the wearer and covers the lower torso of the wearer. Thus, the intermediate crotch region 16 is an area where repeated fluid surges typically occur in the diaper or other disposable absorbent article.

The diaper 100 will typically include a porous, liquid permeable bodyside liner 28 overlying an absorbent body structure 32, and a substantially liquid impermeable outer cover member 30. The absorbent body structure 32 is positioned and attached between the outer cover member 30 and bodyside liner 28. In certain embodiments, a surge layer 48 may be optionally located adjacent the absorbent structure and attached, for example, by way of an adhesive.

The outer cover member 30 and bodyside liner 28 may be separate sheets joined at the respective lateral sides 20a and 20b. Leg elastics 34 may be incorporated along the lateral side margins of the chassis 10 outboard of the absorbent body structure 32 and are configured to draw and hold the chassis 10 against the legs of the wearer. The elastic members 34 are secured to the chassis 10 in an elastically contracted state so that in a normal under-strain condition, the elastic members 34 effectively contract against the chassis. The use of elastic leg members in absorbent articles such as disposable diapers and training pants is widely known and understood in the art.

Various materials are available and known in the art for use as the outer cover member 30. Constructions of the outer cover member 30 may comprise a woven or non-woven fibrous web layer which has been totally or partially constructed or treated to impart the desired levels of liquid impermeability to selected regions that are adjacent or proximate the absorbent body. Alternatively, a separate liquid impermeable material could be associated with the absorbent body structure 32. The outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover member 30 typically provides the outermost layer of the article, optionally the article may include a separate outer cover component member which is additional to the outer cover member.

The outer cover member 30 may be formed substantially from an elastomeric material. Alternatively, the outer cover member may be formed from a non-elastomeric and non-extendable material, or a non-elastomeric and extensible material. The outer cover member 30 may, for example, be composed of a single layer, multiple layers, laminates, spunbond fabrics, films, meltblown fabrics, elastic netting, microporous web, bonded carded webs or foams comprised of elastomeric or polymeric materials.

Elastomeric nonwoven laminate webs may include a nonwoven material joined to one or more gatherable nonwoven webs, films, or foams. Stretch bonded laminates, neck bonded laminates, and necked stretch bonded laminates are examples of elastomeric composites. "Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,720,415; 4,789,699; 4,781,966; 4,657,802; and 4,655,760, which are incorporated herein by reference in their entirety for all purposes. "Neck-bonded" laminate refers to a composite material having an elastic member that is bonded to a non-extensible member while the non-elastomeric member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes. "Neck stretch-bonded" laminate refers a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety by reference thereto for all purposes. "Reversibly-necked material" refers to a necked material that has been treated while necked to impart memory to the material so that when force is applied to extend the material to pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination or mixtures thereof may be used. The production of reversibly-necked materials is described in U.S. Pat. Nos. 4,965,122 and 4,981,747, which are incorporated herein in their entirety by reference thereto for all purposes. Of particular advantage, a necked stretch bonded laminate can be stretchable in both the machine and cross-machine directions. Nonwoven fabrics are any web of material which has been formed without the use of textile weaving processes which produce a structure of individual fibers which are interwoven in an identifiable repeating manner. Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films or filaments, foams, or meltblown fabrics composed of polyethylene, polypropylene, or polyolefin copolymers, as well as combinations thereof. The outer cover 30 may include materials that have elastomeric or extensible properties obtained through a mechanical process, printing process, heating process, or chemical treatment. For example, such materials may be apertured, creped, neck-stretched, heat activated, embossed, and micro-strained; and may be in the form of films, webs, and laminates.

The bodyside liner 28 may be formed from any one or combination of suitable materials known in the art. Various woven and nonwoven fabrics can be used as the bodyside liner 28. For example, the material may include a meltblown web, a spunbonded web, or a bonded-carded-web composed of synthetic continuous or discrete polymer fibers and/or natural fibers, a pattern bonded spunbonded web, airlaid web, or bonded carded web, as well as combinations thereof. The various fabrics can be composed of natural fibers, synthetic fibers or combinations thereof. In particular aspects, the material may be comprised of polymer fibers, networks, laminates, liquid permeable films, cellulosic fibers, rayon, water swellable gels, as well as combinations thereof. Suitable polymers can include polypropylene, polyethylene, polyester, and bicomponent materials composed of these polyolefins. The liner may be elastomeric or extensible or both.

The liner 28 may be composed of a substantially hydrophobic material, and the hydrophobic material may optionally be treated with a surfactant or otherwise processed to impart a desired level of wettability and hydrophilicity. In a particular embodiment of the invention, the material can be a nonwoven, spunbond polypropylene fabric. The fabric can be surface treated with an operative amount of surfactant, such as about 0.6% AHCOVEL Base N62 surfactant, available from ICI Americas, a business having offices located in Wilmington, Del. The surfactant can be applied by any conventional means, such as spraying, dipping, printing, brush coating or the like. The fibers forming the nonwoven material may be mono-component, bi-component, or multi-component fibers, and combinations thereof.

The bodyside liner 28 may include blends or laminates of fibers, scrim, webs, and films with perforations, apertures, creping, heat activation, embossing, micro-straining, chemical treatment, or the like, as well as combinations thereof.

The article 100 may incorporate separate containment flaps 58 attached to the chassis 10 at the waistband portions 11, 17 and along a longitudinal side thereof outboard of the absorbent structure 32. The flaps 58 may contain elastic members 36 along at least a portion of their free laterally inward side 62. The construction of such containment flaps 58 is well known to those skilled in the art and need not be described in detail. Suitable constructions and arrangements for the containment flaps 58 are described, for example, in U.S. Pat. No. 4,704,116, which is incorporated herein by reference for all purposes.

The absorbent body structure 32 can be any structure or combination of components which are generally compressible, conformable, non-irritating to a wearer's skin, and capable of absorbing and retaining liquids and certain body wastes. The structure 32 may be extensible or elastomeric. For example, the structure 32 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from U.S. Alliance of Childersburg, Ala., and is a bleached, highly absorbent wood pulp containing primarily soft wood fibers. The absorbent materials may be formed into a web structure by employing various conventional methods and techniques. For example, the absorbent web may be formed with a dry-forming technique, an air-forming technique, a wet-forming technique, a foam-forming technique, or the like, as well as combinations thereof. Methods and apparatus for carrying out such techniques are well known to those skilled in the art.

As a general rule, the superabsorbent material is present in the absorbent web in an amount of from about 0 to about 90 weight percent based on total weight of the web. The web may have a density within the range of about 0.10 to about 0.35 grams per cubic centimeter.

Superabsorbent materials are well known to those skilled in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company of Midland, Mich.

After being formed or cut into a desired shape, the absorbent web material may be wrapped or encompassed by a suitable wrap that aids in maintaining the integrity and shape of the absorbent structure 32.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. Nos. 4,100,324; 5,284,703; and 5,350,624, which are incorporated herein by reference in their entirety for all purposes.

The absorbent body structure 32 may include an elastomeric coform absorbent web material, for example as described in U.S. Pat. Nos. 4,663,220 and 4,741,949. In particular aspects, the elastomeric coform material can have an overall coform basis weight which is at least a minimum of about 50 g/m². The coform basis weight can alternatively be at least about 100 g/m² and can optionally be at least about 200 g/m² to provide improved performance. In addition, the coform basis weight can be less than about 1200 g/m². Alternatively, the coform basis weight can be less than about 900 g/m², and optionally, can be less than about 800 g/m² to provide improved benefits. These values are important because they can provide the absorbent body structure with desired stretchability and structural stability without excessively degrading the physical properties or the liquid-management functionalities of the absorbent body structure. Retention portions having excessively low proportions of elastomeric coform material may not be sufficiently stretchable. An absorbent web material having excessively large amounts of elastomeric coform materials can exhibit an excessive degradation of their absorbency functionalities, such as an excessive degradation of intake, distribution and/or retention properties.

Other examples of elastomeric absorbent structures are described in U.S. Pat. No. 6,362,389, incorporated herein by reference in its entirety for all purposes.

The absorbent web material utilized in the absorbent body structure 32 is also selected so that the individual absorbent body structure possesses a particular individual total absorbency depending on the intended article of use. For example, for infant care products, the total absorbency can be within the range of about 20 to 900 grams of 0.9 wt % saline, and can typically be about 500 grams of saline. For adult care products, the total absorbency can be within the range of about 400 to 2000 grams of saline, and can typically be about 1300 grams of saline.

As described, the absorbent body structure 32 may also include a surge management layer 48 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. The surge layer can be located below the bodyside liner layer 28. Alternatively, the surge layer may be located on the body facing surface of the bodyside liner 28. Examples of suitable surge management layers are described in U.S. Pat. Nos. 5,486,166 and 5,490,846. Other suitable surge management materials are described in U.S. Pat. No. 5,820,973. The entire disclosures of these patents are hereby incorporated by reference in their entirety for all purposes.

Referring to the figures in general, an absorbent article 100 according to the invention includes a waistband structure 66 attached to at least one of the front and back waist regions 11, 17. The waistband structure includes a filler material 68 extending across at least one of the front and back waist regions 11, 17 and a waistband material 67 positioned over the filler material. The filler material may be placed over or under the liner. In other embodiments the waistband structure may be an integral structure composed of both a filler material 68 and a waistband material 67.

The filler material 68 may be a single layer or multiple layers and can be selected from lofty nonwoven materials, laminates, spunbond fabrics, films, meltblown fabrics, elastic netting, microporous web, bonded carded webs, absorbent core materials, surge materials, or foams comprised of elastomeric or polymeric materials or cellulosic materials such as tissue. The filler material may also be combinations of the above materials. Desirably, the filler material 68 is a soft, lofty material that may substantially fill in the area between the elastomeric material and back waist regions to provide a gasketing function and prevent leakage.

The waistband material 67 may be either an elastomeric material or a non-elastomeric material. The waistband material 67 is desirably a non-elastomeric material in situations where waistbands with low tension are beneficial. For example, non-elastomeric materials are useful for absorbent articles for newborn babies or when enough support for the absorbent article is provided by elastic fasteners.

In other embodiments, the waistband structure 66 includes a suitable elastomeric material for the waistband material 67. "Elastomeric," "elastic," and "elasticized" refer to a material or composite which can be elongated by at least 25% of its relaxed length and which will recover, upon release of the applied force, at least 0% of its elongation. It is generally preferred that the elastomeric material or composite be capable of being elongated by at least 100%, more preferably by at least 300%, of it relaxed length and recover at least 50% of its elongation. An elastomeric material is an extendable material having recovery properties. Suitable elastomeric materials can include, for example, elastic strands, Lycra elastics, elastic films, nonwoven elastic webs, meltblown or spunbond elastomeric fibrous webs, as well as combinations thereof. Examples of elastomeric materials include ESTANE® elastomeric polyurethanes (available from BF Goodrich & Co. located in Cleveland, Ohio), PEBAX elastomers (available from AtoChem located in Philadelphia, Pa.), HYTREL® elastomeric polyester (available from E. I. DuPont de Nemours located in Wilmington, Del.), KRATON® elastomer (available from Shell Chemical Company located in Houston, Tex.), or the like, as well as combinations thereof. A suitable elastomeric material for the waistband structure 66 may comprise a stretch-thermal laminate, a neck-bonded laminate, a reversibly-necked laminate, or a stretch-bonded laminate material. Methods of making such materials are described, for example, in U.S. Pat. Nos. 4,663,220; 5,226,992; and EP Application No. 0 217 032, all of which are incorporated herein by reference in their entirety for all purposes.

In the disposable diaper embodiment illustrated in FIG. 1, the waistband structure 66 is attached only to the back waist region 12. It should be appreciated, however, that an article having a waistband structure 66 attached at the front and back waist regions is within the scope of the absorbent article described herein.

It has been found that a waistband structure 66 attached across the transverse width of the chassis 10 at a waist region simplifies the manufacturing and assembly process of the article 100, and enables more precise prediction and control of the performance of an elastomeric waistband.

The waistband material 67 may be formed of any number of suitable elastomeric materials, as described below, and will have a generally known degree of elasticity. Elastomeric waistbands are typically designed to ensure a comfortable and secure fit of the product under normal use conditions. Waistbands with an excessively high tension of the elastic elements result in an uncomfortable fit, red-marking, and/or difficulty in pulling a pant-like structure up or down. On the other hand, a waistband portion with too low of a tension results in a substantial loss of elasticity of the waistband portion for repeated cycles of the article, or as the elastomeric materials experience stress relaxation in use. This concern is also relevant with training pant articles wherein the user typically pulls the article down and back up to go to the bathroom, etc. The loss of elasticity is also an issue with disposable diapers wherein the diaper may be removed to check whether it has been soiled or wetted. To compensate for potential loss of elasticity under normal use conditions, manufacturers typically incorporate waist elastics with a relatively high tension. However, this may lead to product comfort issues. This is particularly true if the elastomeric portions of the waistband do not span the entire circumference of the waist opening of the article, but are provided in discrete transversely extending sections or portions across the waist opening. With this type of arrangement, the tension forces are not distributed evenly across the waistband and may negatively affect the fit or the article.

The waistband structure 66 is attached across the waist region of the article 100 between the lateral sides 20a and 20b via a bond pattern 70. This results in an elastomeric waistband portion extending between the lateral sides 20a and 20b and attached or joined together to the waist region by conventional suitable attachment methods such as adhesive bonds, sonic bonds, thermal bonds, pinning, stitching or any other attachment technique known in the art, as well as combinations thereof.

By varying the attachment or bond points in the longitudinal direction across the waistband structure 66 and waist region materials, a z-directional height of the elastomeric waistband portion can be varied across the article 100 between the lateral sides 20a and 20b. In other words, by varying the location of the joined or bonded surface area across the waistband structure 66 and waist region 12, the z-directional height or topography of the waistband portion can be adjusted. The z-directional height, H, can also be altered by the shape of the waist and attachment areas, attachment of the waistband structure to non-extensible chassis pieces, and intentional non-attachment of the waistband structure to non-extensible chassis areas.

Desirably, the z-directional height, H, or topography created by the bonded waistband structure provides a softer more pliable waistband resulting in a more comfortable fit for the user. The filler material 68 provides a more cushioned waistband than previously designed waistbands. In addition, the z-directional height, H, or topography provides the wearer or caregiver with a perception that the waistband will be softer.

In the illustrated embodiment, the waistband structure 66 is defined by a band of the waistband material 67 attached to the waist region 12 with a defined bond pattern 70. The waistband structure is bonded to the waist region 11 of the article with a generally uniform bond pattern between the lateral sides 20a and 20b. Referring to FIGS. 1-4, it can be seen that the bond pattern 70 desirably varies in the longitudinal direction across the width of the waistband portion between the lateral sides 20a and 20b. Such a bond pattern 70 is illustrated. It should be appreciated that virtually any configuration of bond shapes or patterns may be used to define the varying bond pattern position in the longitudinal direction across the waistband region between the lateral sides 20a and 20b of the article 100. In the embodiments shown, bond points 72 are defined by generally circular bond points. For example, the bond points 72 are substantially continuous with little spacing therebetween. Typically, the spacing between each bond point 72 should be less than about 10 mm, and more desirably between about 1 and about 5 mm. This substantially continuous pattern reduces the vertical channels that could exist between bond points and helps to prevent leakage creating a gasket function.

Thus, the waistband structure 66 provides a filler material 68 that may substantially fill in the area between the waistband material 67 and back waist regions 17 to provide a gasketing function and reduction of vertical channels through the waistband to prevent leakage. In addition to providing an actual gasketing function, the bond pattern 70 provides a visual cue to the wearer or caregiver of a gasketing function.

Figure 3:
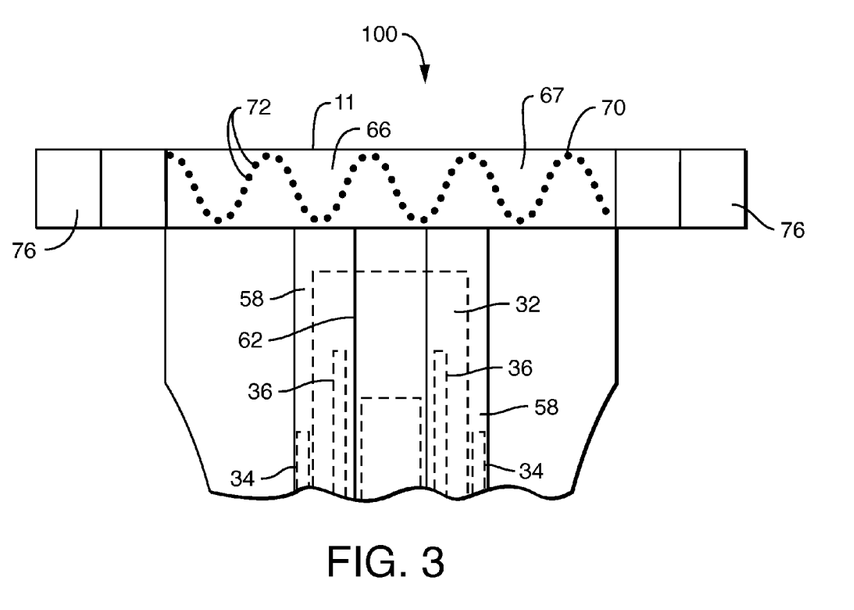
FIG. 3 illustrates a partial bodyside plan view of the waistband region of an alternative embodiment of the absorbent article.
Figure 4:
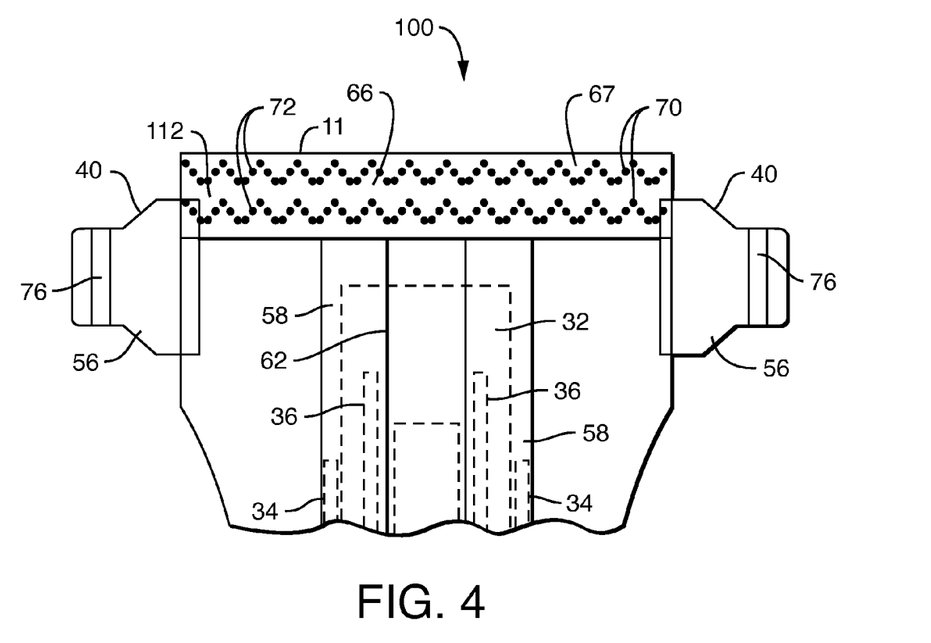
FIG. 4 illustrates a partial bodyside plan view of the waistband region of an alternative embodiment of the absorbent article.
Figure 5:
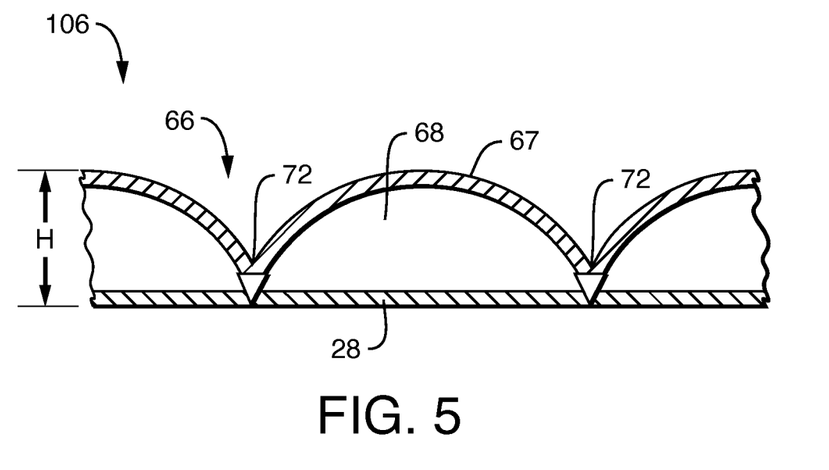
FIG. 5 illustrates a partial cross-sectional view of the longitudinal, lengthwise direction of the waistband region of the absorbent article in FIG. 1.

Desirably, the bond pattern 70 may have a wave pattern having at least one peak 75 and one valley 74 as illustrated in FIGS. 3 and 4, respectively. Typically, a length between the peak 75 and the valley 74 in the bond pattern is between 5 and 100 mm. The bond pattern 70 may be a repeating pattern selected from a sinusoidal, triangle, square or sawtooth pattern. The bond pattern may have an orientation pattern of a wave with a half cycle, one cycle, one and a half cycles, two cycles, or more depending on the overall desired change in longitudinal direction of the bond pattern.

As illustrated in FIGS. 1 and 4, the waistband structure 66 is bonded to the waist region 11 of the article with a multiple series 112 of bond patterns 70 between the lateral sides 20a and 20b. While illustrated in FIG. 4 that the multiple series of bond patterns have the same size and shape, one skilled in the art can appreciate that the size and shape of each bond pattern can vary to provide different visual effects.

Figure 6:
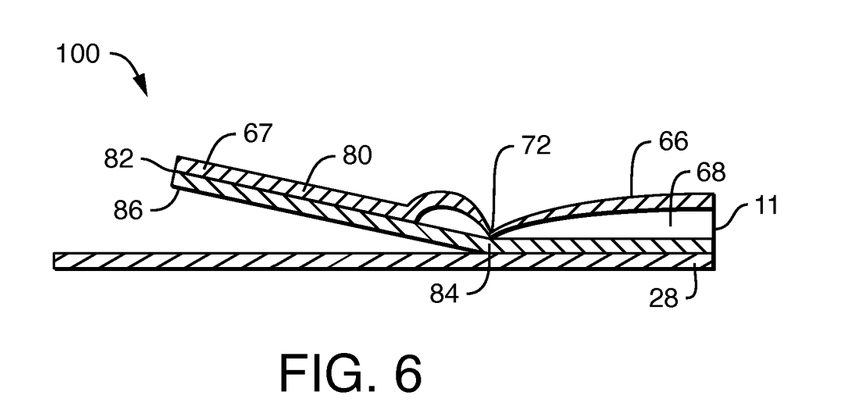
FIG. 6 illustrates a partial cross-sectional view of the lateral, transverse cross-direction of the waistband region of the absorbent article in FIG. 1.

When using an elastomeric material, the waistband structure 66 may be attached to the chassis material between the lateral sides 20a and 20b in a tensioned state, such that upon releasing the elastomeric waistband material 67, the front or back waist region material 11, 17 is gathered resulting in a stretchable or extendable waistband region. As best seen in FIG. 6, the filler material 68 is not in a tensioned state allowing the filler material to gather and substantially fill into the area between the elastomeric material 67 and the waist region material and provides a z-directional height across the width of the waistband structure 66. The waistband region may be stretchable at least to an extent permitted by the degree of gathering of the waistband region, as is commonly understood by those skilled in the art. In one embodiment, the elastomeric waistband material 68 may be attached in a tensioned state that is less than its maximum elongation such that stretchability of the waistband portion is limited by the degree of gathering of the waistband materials, and not the elastomeric waistband material 68.

As illustrated in FIGS. 1 and 6, the waistband structure 66 may further comprise a waist pocket member 80 extending laterally and longitudinally to define a barrier flap or pocket section 82. The flap or pocket section of the waistband structure includes a substantially fixed edge portion 84 secured to the waist region of the absorbent article and a movable edge portion, which is typically longitudinally spaced from the fixed edge portion by a selected distance. Typically this fixed edge portion 84 will be the bond pattern 70 attaching the waistband structure to the waist region. The pocket section thereby defines a waist dam and waist flap construction. The pocket section 82 may also contain a substantially liquid impermeable layer 86 attached to the waistband structure to enhance the leakage protection.

This embodiment, as illustrated in FIG. 1, includes an additional series of a bond pattern 70, but this bond pattern 70 does not extend all the way across the waistband structure 66. Including a bond pattern that does not extend across the entire width of the waistband structure 66 further defines the pocket section 82 and further enhances leakage protection. This also increases the visual perception to a user that the absorbent article will provide a leakage benefit.

A fastening system 40 is operably attached to and joined to the article at either or both of the laterally opposed end regions and at least one of the front and back waist regions. A cooperating side panel member 56 can be associated with each fastening system and may be constructed to be elastomeric or non-elastomeric. In addition, an attachment tab 76 can be attached to extend laterally outboard from each side panel member 56.

Alternatively, the elastomeric band 67 of the waistband structure 66 may extend laterally outboard of the sides 20a and 20b of the chassis 10 defining attachment tabs 76, as can be particularly seen in FIG. 3.

It should be understood that various other embodiments, modifications, and equivalents to the embodiments of the absorbent article described herein which, after reading the description herein, may suggest themselves to those skilled in the art without departing from the scope and spirit of the present claims.

We claim:
1. An absorbent article, comprising:
a chassis having a front waist region, a back waist region, and a crotch region extending between the front and back waist regions;
an outer cover member and a bodyside liner extending between the front and back waist regions;
an absorbent body structure between the outer cover member and the bodyside liner;
a waistband structure comprising a filler material and a waistband material, the waistband structure extending across at least one of the front and back waist regions; and wherein the waistband structure is bonded to the at least one of the front and back waist regions via a bond pattern, the bond pattern varying position in the longitudinal direction and having a plurality of peaks and valleys across the respective waist region, and wherein a z-directional height of the waistband structure varies on the respective waist region.

2. The absorbent article of claim 1 wherein the filler material is selected from lofty nonwoven materials, laminates, spunbond fabrics, films, meltblown fabrics, elastic netting, microporous web, bonded carded webs, absorbent core materials, surge materials, or foams comprised of elastomeric or polymeric materials, cellulosic materials, and combinations thereof.

3. The absorbent article of claim 1 wherein the filler material is a lofty nonwoven material.

4. The absorbent article of claim 1 wherein the bond pattern is a repeating wave pattern selected from a sinusoidal, triangle, square or sawtooth pattern.

5. The absorbent article of claim 1 wherein a distance between one of the peaks and the valleys in the bond pattern is between 5 and 100 mm.

6. The absorbent article of claim 1 wherein the bond pattern is a continuous pattern of discrete bond points, wherein a distance between successive bond points is less than about 10 mm.

7. The absorbent article of claim 1 further comprising a waist pocket flap extending longitudinally from the waistband structure.

8. The absorbent article of claim 1 wherein the waistband material comprises an elastomeric material positioned over the filler material.

9. An absorbent article comprising:
a chassis having a front waist region, a back waist region, and a crotch region extending between the front and back waist-regions;
an outer cover member and a bodyside liner extending between the front and back waist regions;
an absorbent body structure between the outer cover member and the bodyside liner;
a waistband structure extending across at least one of the front and back waist regions, the waistband structure comprising a filler material and an elastomeric material; and
wherein the waistband structure is bonded to the at least one of the front and back waist regions via multiple series of bond patterns, each series of bond patterns defining a wave pattern across the respective waist region and wherein a z-directional height of the waistband structure varies on the respective waist region.

10. The absorbent article of claim 9 wherein each series of bond pattern is a repeating wave pattern selected from a sinusoidal, triangle, square or sawtooth pattern.

11. The absorbent article of claim 9 wherein each series of bond pattern comprises at least one peak and one valley across the respective waist region and a distance between the peak and the valley in each bond pattern is between 5 and 100 mm.

12. The absorbent article of claim 9 wherein each series of bond patterns is a continuous pattern of discrete bond points, wherein a distance between successive bond points is less than about 10 mm.

13. The absorbent article of claim 9 wherein the filler material is selected from lofty nonwoven materials, laminates, spunbond fabrics, films, meltblown fabrics, elastic netting, microporous web, bonded carded webs, absorbent core materials, surge materials, or foams comprised of elastomeric or polymeric materials, cellulosic materials, and combinations thereof.

14. The absorbent article of claim 9 wherein the filler material is a lofty nonwoven material.

15. An absorbent article, comprising:
a chassis having a front waist region, a back waist region, and a crotch region extending between the front and back waist-regions;
an outer cover member and a bodyside liner extending between the front and back waist regions;
an absorbent body structure between the outer cover member and the bodyside liner;
a waistband structure extending across at least one of the front and back waist regions and bonded to the at least one of the front and back waist regions via a bond pattern, the waistband structure comprising a filler material and a waistband material;
wherein the bond pattern is a repeating wave pattern across the respective waist region resulting in a z-directional height of the waistband structure varying across the respective waist region.

16. The absorbent article of claim 15 wherein the bond pattern is a continuous pattern of discrete bond points, wherein a distance between successive bond points is less than about 10 mm.

17. The absorbent article of claim 15 wherein the filler material is selected from lofty nonwoven materials, laminates, spunbond fabrics, films, meltblown fabrics, elastic netting, microporous web, bonded carded webs, absorbent core materials, surge materials, or foams comprised of elastomeric or polymeric materials, cellulosic materials, and combinations thereof.

18. The absorbent article of claim 15 wherein the filler material is a lofty nonwoven material.

19. The absorbent article of claim 15 wherein the waistband material is an elastomeric material.

* * * * *